United States Patent

Davidovitz et al.

[11] Patent Number: 5,226,206
[45] Date of Patent: Jul. 13, 1993

[54] TOOTHBRUSH

[75] Inventors: Zvi Davidovitz, Rishon Lezion; Israel Ramot, Kfar Saba, both of Israel

[73] Assignee: A to Z Technology Ltd., Ramat Gan, Israel

[21] Appl. No.: 957,856

[22] Filed: Oct. 8, 1992

[30] Foreign Application Priority Data

Oct. 11, 1991 [IL]  Israel ........................................ 99717

[51] Int. Cl.$^5$ ........................ A61C 17/34; A46B 13/02
[52] U.S. Cl. ............................................. 15/22.1; 15/28
[58] Field of Search ................... 15/22.1, 22.2, 22.4, 15/28, 29; 433/216

[56]  References Cited

U.S. PATENT DOCUMENTS

| | | | |
|---|---|---|---|
| 4,156,620 | 5/1979 | Clemens | 15/22.1 |
| 4,989,287 | 2/1991 | Scherer | 15/22.1 |
| 5,120,225 | 6/1992 | Amit | 15/22.1 |

Primary Examiner—Edward L. Roberts
Attorney, Agent, or Firm—Benjamin J. Barish

[57] ABSTRACT

A toothbrush includes a bristle holder oscillatably mounted within a brush head, and a carrier assembly carrying the bristle holder and reciprocatable with it within the brush head by a motor; and a coupling between the bristle holder and the brush head effective to oscillate the bristle holder upon its reciprocation by the motor.

20 Claims, 2 Drawing Sheets

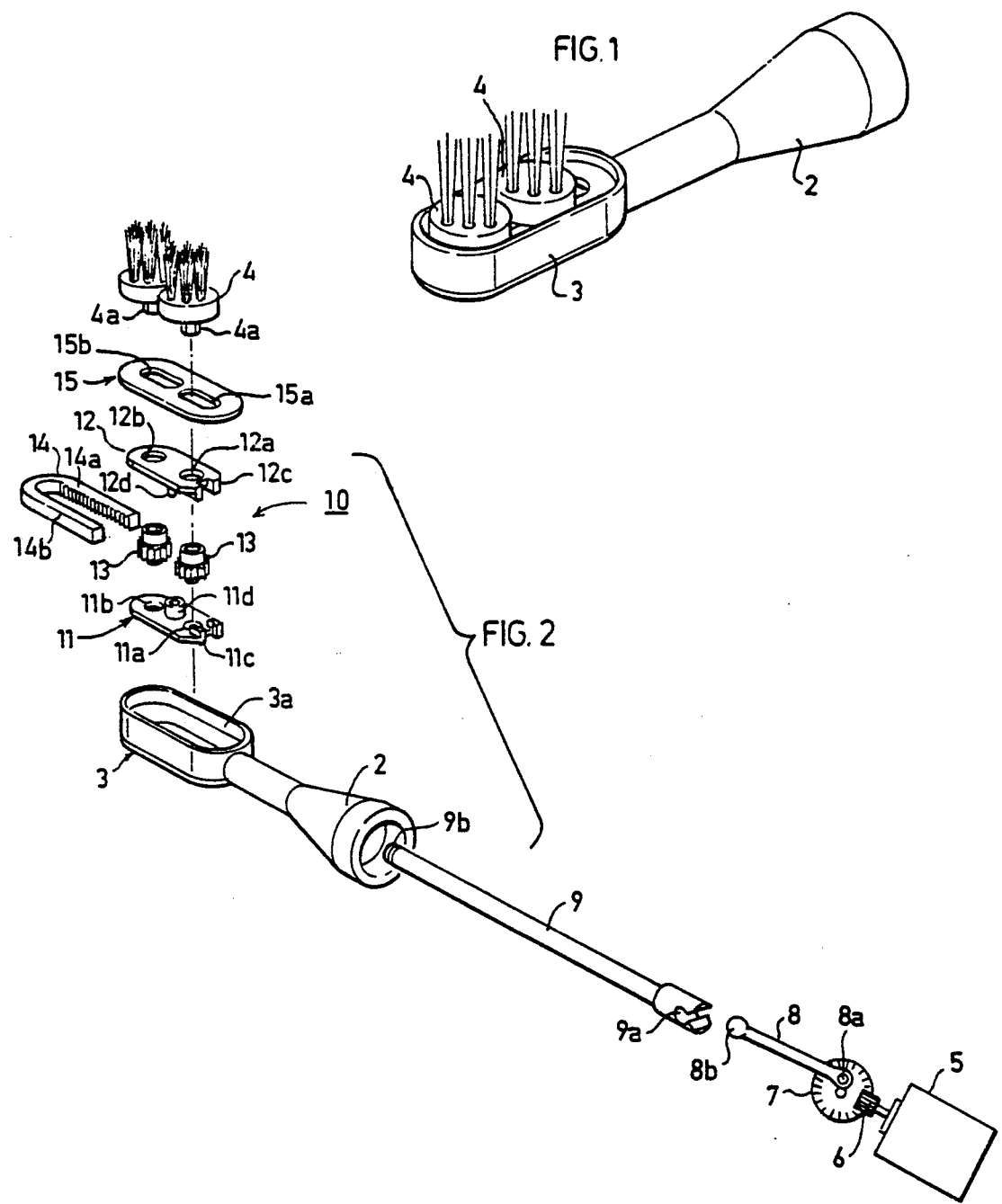

TOOTHBRUSH

FIELD AND BACKGROUND OF THE INVENTION

The present invention relates to toothbrushes, and particularly to a motor-driven type toothbrush which includes one or more oscillating bristle holders.

In recent years, motor-driven toothbrushes with oscillating bristle holders have become very popular. Such toothbrushes include a handle at one end, a brush head at the opposite end, at least one (usually more) bristle holder oscillatably mounted within the brush head, a motor within the handle, and a transmission assembly coupling the motor to the bristle holder to oscillate it upon energization of the motor. The oscillating movement of the bristle holders has been found effective to enhance the removal of plaque, namely the soft amorphus deposit that accumulates on the surfaces of teeth.

OBJECTS AND BRIEF SUMMARY OF THE INVENTION

An object of the present invention is to provide a novel toothbrush of the foregoing type which further enhances the removal of plaque.

According to the present invention, there is provided a toothbrush as set forth above characterized in that the transmission includes a carrier assembly carrying the bristle holder and reciprocatable therewith within the brush head by the motor, and coupling means between the bristle holder and the brush head and effective to oscillate the bristle holder upon its reciprocation by the motor.

It will thus be seen that a toothbrush constructed in accordance with the foregoing features not only oscillates the bristle holder about its own longitudinal axis, but also reciprocates the bristle holder in a direction perpendicular to its longitudinal axis. Such a dual-motion action of the bristle holder in the toothbrush further enhances the plaque removal when using the toothbrush for brushing teeth.

According to further features in the preferred embodiment of the invention described below, the coupling means comprises a circular gear non-rotatably coupled to the bristle holder and meshing with a rack fixed to the brush head. More particularly, in the described preferred embodiment, the circular gear includes a circular stem at one end received within a circular opening formed in the carrier assembly, and a non-circular socket at its opposite end receiving a non-circular stem formed in the bristle holder.

According to further features in the described preferred embodiment, the carrier assembly carries at least two bristle holders in alignment with the handle, each bristle holder including a circular gear non-rotatably coupled to its bristle holder and meshing with a rack fixed to the brush head. The provision of two (or more) bristle holders having the above-described combined-motions even further enhances plaque removal.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a three-dimensional view illustrating one form of toothbrush constructed in accordance with the present invention;

FIG. 2 is an exploded view illustrating the main components of the toothbrush of FIG. 1;

DESCRIPTION OF PREFERRED EMBODIMENTS

Figure 3:
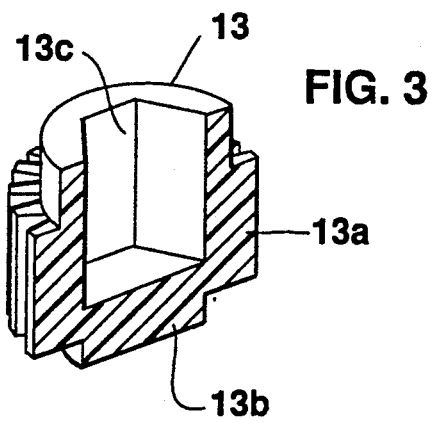
FIG. 3 is an enlarged view illustrating one of the circular gears in the toothbrush of FIGS. 1 and 2.
Figure 4:
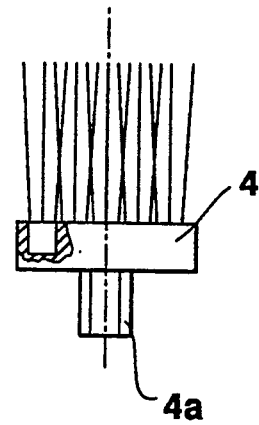
FIG. 4 is an end view, partly in section, illustrating one of the bristle holders in the toothbrush of FIGS. 1 and 2.
Figure 5:
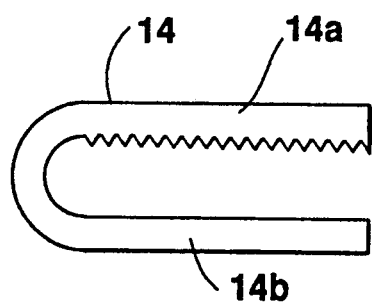
FIG. 5 is a top plan view illustrating the fixed rack within the toothbrush of FIGS. 1 and 2.

The toothbrush illustrated in the drawings comprises a handle 2 at one end, a brush head 3 at the opposite end, and a pair of bristle holders 4 each oscillatably mounted within the brush head; that is, each of the bristle holders 4 is mounted for partial rotary movement, in opposite directions, about its own longitudinal axis. The toothbrush further includes a motor 5 within the handle 2, and a transmission assembly coupling the motor 5 to the bristle holders 4 to oscillate them upon energization of the motor.

The transmission assembly includes a gear 6 fixed to the output shaft of the motor 5 and driving a circular gear 7 having a crank arm 8 eccentrically coupled at one end 8a to gear 7, and coupled at its opposite end 8b to a rod 9 for reciprocating the rod. Rod 9 is formed at one end with a socket 9a receiving a ball formed at end 8b of the crank arm 8; the opposite end of rod 9 is formed with an annular groove 9b which is coupled to a carrier assembly, generally designated 10, carrying the two bristle holders 4.

The carrier assembly 10 includes a lower carrier plate 11, an upper carrier plate 12, and a pair of circular gears 13 oscillatably received between the two plates. Carrier plate 11 is formed with two circular openings 11a, 11b, and with a pair of ribs 11c at one edge; and carrier plate 12 is similarly formed with a pair of circular openings 12a, 12b and with a pair of ribs 12c at one end. Carrier plate 11 is further formed with a cylindrical socket 11d between the two circular openings 11a, 11b; and carrier plate 12 is formed with a depending cylindrical pin 12d which is receivable, with a snap-action, into socket 11d of carrier plate 11 in order to secure the two plates together with the two circular gears 13 in between.

As shown more particularly in FIG. 3, each of the circular gears 13 is formed with peripheral teeth 13a, a circular stem 13b depending from its bottom, and a non-circular socket 13c opening from its top. Its circular stem 13b is rotatably received within its respective circular opening 11a, 11b of the lower carrier plate 11, and the opposite end of the circular gear is rotatably receiving within its respective opening 12a, 12b of the upper carrier plate 12. Its non-circular socket 13c (e.g., a hexagonal socket) is adapted to receive a complementary-configured stem 4a depending from the lower end of the respective bristle holder 4, such that the rotation of a gear 13 will also rotate its respective bristle holder 4.

Carrier assembly 10, including the two gears 13 and their respective bristle holders 4, are reciprocatable within a cavity 3a formed in the brush head 3 towards and away from the motor 5. A U-shaped rack member 14 is fixed within cavity 3a of the brush head 3. Rack member 14 includes a leg 14a formed with teeth meshing with gears 13 of the carrier assembly 10, and with a second parallel leg 14b which is untoothed. Thus, as the carrier assembly 10 is reciprocated by rod 9 within cavity 3a of the brush head 3, the gears 13, meshing with the toothed leg 14a of the U-shaped member 14, oscillate the two bristle holders 4 about their respective axes.

A cover plate 15 closes socket 3a of the brush head. Cover 15 is formed with a pair of openings 15a, 15b for receiving the stems 4a of the two bristle holders 4. As shown in FIG. 2, openings 15a, 15b are elongated in the direction parallel to the longitudinal axis of the handle 2 in order to accommodate the reciprocatory movements of the bristle holders 4.

The operation of the toothbrush will be apparent from the above description. Thus, when motor 5 is energized, the transmission between it and the bristle holders 4 reciprocates the bristle holders within cavity 3a of the brush head 3 towards and away from the motor. As the carrier assembly 10 is thus reciprocated, its gears 13, meshing with the toothed leg 14a of the U-shaped rack member 14 fixed within the brush head cavity 3a, oscillate the two bristle holders about their respective axes; that is, as the carrier assembly 10 including the bristle holders 4 are moved through the forward strokes (away from motor 5), the two gears 13 are rotated clockwise, and as they are moved through their return strokes (towards the motor 5), they are rotated counter-clockwise. Since the two bristle holders 4 are non-rotatably received within the sockets 13c of the gears 13, they are also rotated clockwise during the forward strokes, and counter-clockwise during the return strokes.

It will thus be seen that energization of motor 5 causes the two bristle holders 4 to undergo both oscillatory movements and reciprocatory movements, thereby enhancing the removal of plaque during brushing of the teeth.

Figure 6:
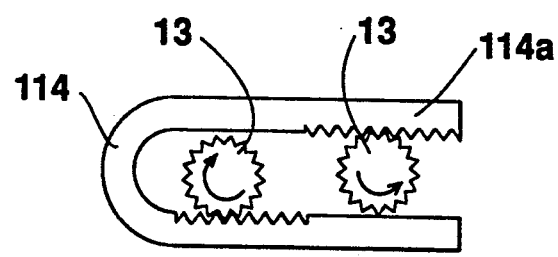
FIG. 6 is a view similar to that of FIG. 5 but illustrating a modification in the construction of the rack.

FIG. 6 illustrates a modification in the construction of the U-shaped rack member, therein designated 114. Thus, one leg 114a of the rack member is formed with teeth for only a part of its length, cooperable with gear 113 of one brush holder; whereas the other leg 114b of the rack member is formed with teeth cooperable with gear 113 of the other brush holder. Thus, in the modification illustrated in FIG. 6, the energization of motor 5 will cause the two bristle holders to oscillate in opposite directions, rather than in the same direction as in the arrangement illustrated in FIGS. 1–5.

Many other modifications may be made. For example, instead of using a rack (14 or 114) for oscillating the bristle holders 4 via gears (13), the rack may be friction-coupled to rollers to oscillate the bristle holders. In addition, the end of rod 9 formed with the socket 9a for receiving the ball 8b may be formed with a short longitudinal split to facilitate the snap-fitting of the ball into the socket. Many other variations, modifications and applications of the invention will be apparent.

What is claimed is:

1. A toothbrush comprising: a handle at one end, a brush head at the opposite end, at least one bristle holder oscillatably mounted within said brush head, a motor within said handle, and a transmission assembly coupling said motor to said bristle holder to oscillate the bristle holder upon energization of the motor; characterized in that said transmission includes a carrier assembly carrying said bristle holder and reciprocatable therewith within said brush head by said motor; and coupling means between said bristle holder and said brush head effective to oscillate said bristle holder upon its reciprocation by said motor.

2. The toothbrush according to claim 1, wherein said carrier assembly is reciprocatable towards and away from said handle.

3. The toothbrush according to claim 2, wherein said carrier assembly carries at least two bristle holders in alignment with said handle.

4. The toothbrush according to claim 2, wherein said coupling means comprises a circular gear non-rotatably coupled to said bristle holder and meshing with a rack fixed to said brush head.

5. The toothbrush according to claim 4, wherein said circular gear includes a circular stem at one end received within a circular opening formed in said carrier assembly, and a non-circular socket at its opposite end receiving a non-circular stem formed in said bristle holder.

6. The toothbrush according to claim 4, wherein said carrier assembly includes an inner plate formed with said circular opening, an outer plate formed with a circular opening clearingly receiving said non-circular stem of the bristle holder, and fastening means for fastening the two plates together with said circular gear in between.

7. The toothbrush according to claim 6, wherein said fastening means comprises a cylindrical socket on one of said plates receiving with a snap-action a cylindrical pin on the other of said plates.

8. The toothbrush according to claim 4, wherein said carrier assembly carries at least two bristle holders in alignment with said handle, each bristle holder including a circular gear non-rotatably coupled to its bristle holder and meshing with a rack fixed to said brush head.

9. The toothbrush according to claim 8, wherein said rack is part of a two-legged U-shaped member fixed within said brush head.

10. The toothbrush according to claim 9, wherein one of the legs of the U-shaped member is formed with teeth meshing with the circular gears of both of said bristle holders.

11. The toothbrush according to claim 9, wherein a part of each of the two legs of the U-shaped member is formed with teeth each part meshing with the circular gears of one of said bristle holders.

12. The toothbrush according to claim 1, further including a cover formed with an opening for each of said bristle holders and elongated in the direction of reciprocation of the carrier assembly.

13. The toothbrush according to claim 1, wherein said transmission further includes a gear rotatable by said motor, and a crank arm eccentrically coupled at one end to said gear and at the opposite end to said carrier assembly.

14. The toothbrush according to claim 13, wherein said transmission further includes a rod having one end coupled to said crank arm and the opposite end coupled to said carrier assembly 15. The toothbrush according to claim 14, wherein said one end of the rod is coupled to said crank arm by means of a ball formed at the end of the crank arm received within a socket formed in the respective end of the rod.

16. The toothbrush according to claim 14, wherein the opposite end of the rod is coupled to said carrier assembly by means of an annular groove formed in the rod receiving a pair of ribs formed in the respective end of the carrier assembly.

17. A toothbrush comprising:
a handle at one end;
a brush head at the opposite end;
at least one bristle holder oscillatably mounted within said brush head;
a motor within said handle;
and a transmission assembly coupling said motor to said bristle holder to oscillate the bristle holder upon energization of the motor;
said transmission including a carrier assembly carrying said bristle holder and reciprocatable therewith within said brush head by said motor towards and away from said handle;
and coupling means between said bristle holder and said brush head comprising a circular gear non-rotatably coupled to said bristle holder and meshing with a rack fixed to said brush head and effective to oscillate said bristle holder upon its reciprocation by said motor.

18. The toothbrush according to claim 17, wherein said circular gear includes a circular stem at one end received within a circular opening formed in said carrier assembly, and a non-circular socket at its opposite end receiving a non-circular stem formed in said bristle holder.

19. The toothbrush according to claim 17, wherein said carrier assembly includes an inner plate formed with said circular opening, an outer plate formed with a circular opening clearingly receiving said non-circular stem of the bristle holder, and fastening means for fastening the two plates together with said circular gear in between.

20. The toothbrush according to claim 19, wherein said fastening means comprises a cylindrical socket on one of said plates receiving with a snap-action a cylindrical pin on the other of said plates.

* * * * *